United States Patent
Lu

(10) Patent No.: US 11,186,550 B2
(45) Date of Patent: Nov. 30, 2021

(54) SMALL MOLECULE COMPOUND

(71) Applicant: Cerepeut, Inc., Stanford, CA (US)

(72) Inventor: Bingwei Lu, Stanford, CA (US)

(73) Assignee: Cerepeut, Inc., Stanford, CA (US)

( * ) Notice: Subject to any disclaimer, the term of this patent is extended or adjusted under 35 U.S.C. 154(b) by 30 days.

(21) Appl. No.: 16/647,383

(22) PCT Filed: Sep. 12, 2018

(86) PCT No.: PCT/US2018/050689
§ 371 (c)(1),
(2) Date: Mar. 13, 2020

(87) PCT Pub. No.: WO2019/055528
PCT Pub. Date: Mar. 21, 2019

(65) Prior Publication Data
US 2020/0216400 A1    Jul. 9, 2020

Related U.S. Application Data

(60) Provisional application No. 62/558,323, filed on Sep. 13, 2017.

(51) Int. Cl.
C07D 239/95 (2006.01)
A61P 9/10 (2006.01)
A61P 23/00 (2006.01)
A61P 35/00 (2006.01)

(52) U.S. Cl.
CPC .............. *C07D 239/95* (2013.01); *A61P 9/10* (2018.01); *A61P 23/00* (2018.01); *A61P 35/00* (2018.01)

(58) Field of Classification Search
CPC .......... C07D 239/95; A61P 9/10; A61P 23/00; A61P 35/00
See application file for complete search history.

(56) References Cited

U.S. PATENT DOCUMENTS

| 8,450,333 B2 | 5/2013 | Nunnari et al. |
| 8,759,097 B2 | 6/2014 | Qian et al. |
| 9,289,448 B2 | 3/2016 | Lu et al. |
| 9,719,090 B2 | 8/2017 | Lu et al. |
| 9,730,935 B2 | 8/2017 | Lu et al. |
| 10,149,860 B2 | 12/2018 | Lu et al. |
| 2015/0164896 A1 | 6/2015 | Lu et al. |
| 2019/0105341 A1 | 4/2019 | Lu et al. |

FOREIGN PATENT DOCUMENTS

WO    WO 2005/051974    *   6/2005    ........... C07D 239/95

OTHER PUBLICATIONS

Cassidy-Stone, A. et al., "Chemical Inhibition of the Mitochondrial Division Dynamin Reveals Its Role in Bax/Bak-Dependent Mitochondrial Outer Membrane Permeabilization," Developmental Cell, 14:193-204, 2008.
Lee, K-S. et al., "Roles of PINK1, mTORC2, and mitochondria in preserving brain tumor-forming stem cells in a noncanonical Notch signaling pathway." Genes and Development, 27:2642-2647, 2013.
Lenaz, G et al., "Mitochondrial Complex I: Structural and functional aspects." Biochimica et Biophysica Acta, 1757: 1406-1420, 2006.
Scialo, F et al., "Role of Mitochondrial Reverse Electron Transport in ROS Signaling: Potential Roles in Health and Disease." Front. Physiol. 8:428. doi: 10.3389/fphys.2017.00428, 2017, 7 pages.
International Search Report issued in connection with corresponding International Application No. PCT/US2018/050689, dated Nov. 9, 2018, 2 pages.

* cited by examiner

*Primary Examiner* — Alicia L Otton
(74) *Attorney, Agent, or Firm* — Kilpatrick Townsend & Stockton LLP

(57) ABSTRACT

The present invention relates to compositions and methods for the treatment of cancer and other diseases associated with mitochondrial dysfunction, including but not limited to, neurodegenerative disease, brain injuries, and certain non-neurological disorders, using a novel compound CPT-2008 and derivatives thereof.

14 Claims, 11 Drawing Sheets

SMALL MOLECULE COMPOUND

CROSS-REFERENCES TO RELATED APPLICATIONS

The present application claims priority to U.S. Provisional Pat. Appl. No. 62/558,323, filed Sep. 13, 2017, which application is incorporated herein by reference in its entirety.

BACKGROUND OF THE INVENTION

Mitochondria are iconic organelles in eukaryotic cells that are essential for ensuring numerous fundamental physiological processes such as cellular energy production, redox balance, buffering of cellular $Ca^{2+}$ concentration, and hosting important biosynthetic pathways (Wallace 2005). They also govern the cell fate by participating in the apoptosis pathway, a pathway critically in major disease conditions such as cancer and neurodegenerative diseases (Hedskog et al. 2012). The shape, volume, number and distribution of mitochondria within the cells are strictly controlled (Cahill et al. 2006). These parameters critically impact mitochondrial function, especially in the neuromuscular system, where mitochondria adopt strategic intracellular distribution, presumably to satisfy high local energy demands. Thus, the maintenance of a healthy mitochondrial population is essential for cellular and organismal health. To achieve this, cells have developed mechanisms involving a complex system of quality control to remove damaged mitochondria, or to renew them. Defects of these processes can lead to the accumulation of damaged mitochondria and ultimately result in disease conditions (Pickrell and Youle 2015), (Rugarli and Langer 2012).

Mitochondrial dysfunction can affect cellular function in a number of ways (Stepien et al. 2017), (Pieczenik and Neustadt 2007). First of all, as the cellular power plant, mitochondria provide the key source of ATP. Mitochondrial dysfunction will result in cellular energy deficit and impaired maintenance of cellular vitality. Second, mitochondria hosts the electron transport chain involved in oxidative phosphorylation. This process generates reactive oxygen species (ROS) that under basal condition may provide some signaling function, but defective mitochondria are inefficient in the electron transfer process, resulting in elevated ROS production, which can cause damages to all essential macromolecules (proteins, nucleic acids, lipids, etc.). Such oxidative damages have been extensively linked to diseases, especially those age-related diseases (Kauppila et al. 2017). Third, mitochondria are important organelles in maintaining cellular calcium homeostasis (Paillusson et al. 2016). They uptake calcium released from intracellular stores, especially the ER, or calcium resulting from excitation. Dysfunctional mitochondria may alter cellular calcium homeostasis and cause conditions such as ER stress that have been linked to a number of disease conditions (Malhotra and Kaufman 2011). Moreover, mitochondrial calcium is essential for the activities of certain enzymes in the TCA cycle and the electron transport chain (Glancy and Balaban 2012). Therefore, altered mitochondrial calcium homeostasis can lead to mitochondrial energetic deficit. Finally, as gatekeepers of cell life and cell death, mitochondria regulate both apoptotic and necrotic cell death (Galluzzi et al. 2016). Thus at its most extreme, disturbances involving these pathways may trigger untimely cell death and cause degenerative disease. Conversely, the lack of appropriate cell death can lead to inappropriate tissue growth and development of cancers, which are often characterized by altered mitochondrial metabolism.

It is therefore not surprising that a large number of major human diseases, many of which represent urgent unmet medical needs, have been associated with mitochondrial dysfunction. These range from cancer (Wallace 2012) and neurodegenerative diseases such as Alzheimer's disease, Parkinson's disease, and ALS (de Moura et al. 2010), (Lleonart et al. 2017), (Ganguly et al. 2017) to brain injuries such as Stroke, Seizures, Neuropathic pain, Traumatic brain injury, Spinal cord injury, Aneurysm, Subarachnoid hemorrhage (Dawson and Dawson 2017), (Areti et al. 2016), (Sui et al. 2013), (Zsurka and Kunz 2015), (Cahill et al. 2006), (Hiebert et al. 2015), (Arun et al. 2016), and certain non-neurological disorders, for example Sepsis, Acute kidney injury, Cardiorenal syndrome, Cardiac Ischemia-reperfusion injury, Pulmonary arterial hypertension, Chronic obstructive pulmonary disease, and vasoconstriction (Stepien et al. 2017), (Lesnefsky et al. 2017), (Emma et al. 2016), (Lerner et al. 2016), (Sutendra and Michelakis 2014), (Ratliff et al. 2016). However, the exact mechanisms by which defective mitochondria lead to the diverse disease conditions remain to be elucidated, and it remains to be seen whether novel mitochondrial medicine could be developed to treat a number of devastating and pervasive diseases.

SUMMARY OF THE INVENTION

Disclosed herein are composition for treating or preventing diseases associated with mitochondrial dysfunction. The compositions include CPT-2008 (i.e., 6-chloro-3-(2,4-dichloro-5-methoxyphenyl)-2-mercapto-7-methoxyquinazolin-4(3H)-one), pharmaceutically acceptable salts thereof, or derivatives thereof.

Also disclosed herein are methods for preventing or treating diseases associated with mitochondrial dysfunction. The methods include administering an effective amount of CPT-2008 or a composition containing an effective amount of CPT-2008, or a derivative thereof, to a subject in need thereof (e.g., in a human or other mammal).

Aspects of the present disclosure include, but are not limited to, the appended claims and the following exemplary embodiments:

1. A compound according to Formula I:

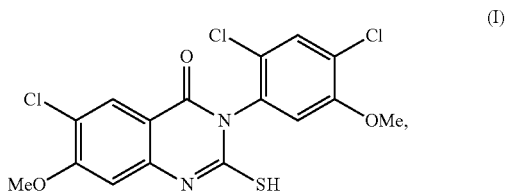 [SMILES: COc1cc(-n2c(S)nc3cc(OC)c(Cl)cc3c2=O)c(Cl)cc1Cl]

or a pharmaceutically acceptable salt thereof.

2. A pharmaceutical composition for treating a disease or condition associated with mitochondrial dysfunction, the composition comprising the compound of embodiment 1 according to Formula I, a pharmaceutically acceptable salt thereof, or a derivative thereof, and a pharmaceutically acceptable carrier.

3. A method for treating a disease or condition associated with mitochondrial dysfunction, the method comprising an effective amount of the compound of embodiment 1 or an effective amount of the composition of embodiment 2 to a subject in need thereof.
4. The method of embodiment 3, wherein the effective amount is a therapeutically effective amount.
5. The method of embodiment 3, wherein the effective amount is a prophylactically effective amount.
6. The method of embodiment 3, wherein the disease is cancer.
7. The method of embodiment 6, wherein the cancer is T-acute lymphoblastic leukemia (T-ALL), small cell lung cancer (SCLC), non-small cell lung cancer (NSCL), glioblastoma, colorectal cancer, breast cancer, or ovarian cancer.
8. The method of embodiment 3, wherein the disease is a neurodegenerative disease.
9. The method of embodiment 8, wherein the neurodegenerative disease is Parkinson's disease, Alzheimer's disease, amyotrophic lateral sclerosis, or Huntington's disease.
10. The method of embodiment 3, wherein the condition is a brain condition.
11. The method of embodiment 10, wherein the brain condition is stroke, seizure, neuropathic pain, traumatic brain injury, spinal cord injury, aneurysm, or subarachnoid hemorrhage.
12. The method of embodiment 3, wherein the disease or condition is a non-neurological disorder.
13. The method of embodiment 14, wherein the non-neurological disorder is sepsis, acute kidney injury, cardiorenal syndrome, cardiac ischemia-reperfusion injury, pulmonary arterial hypertension, chronic obstructive pulmonary disease, or vasoconstriction.
14. The method of embodiment 3, wherein the condition is human aging caused by mitochondrial dysfunction.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION OF THE INVENTION

I. Field of the Invention

Figure 1:
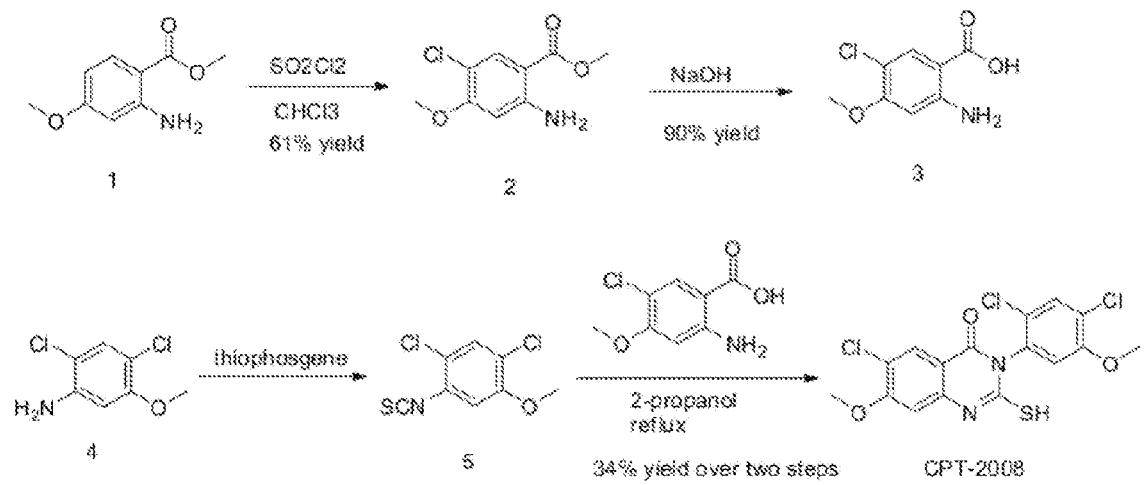
FIG. 1 shows a route for the chemical synthesis of CPT-2008
Figure 2:
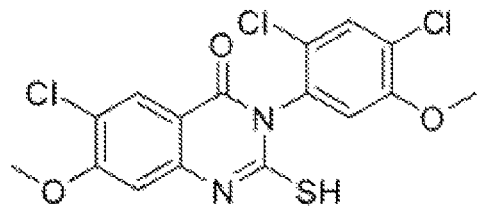
FIG. 2 shows the chemical structure of CPT-2008
Figure 3:
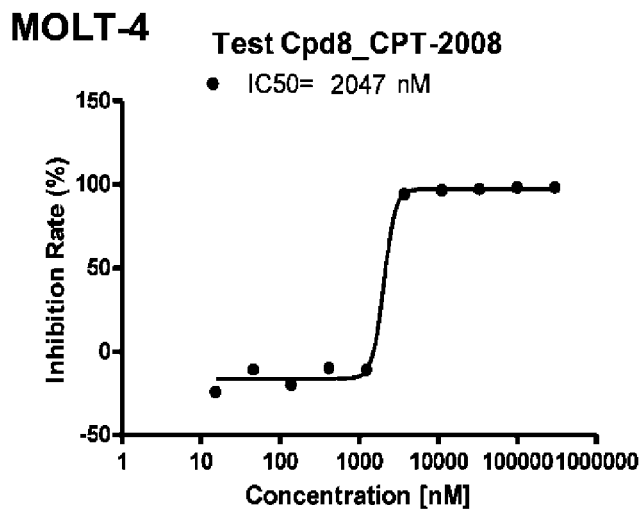
FIG. 3 shows the efficacy of CPT-2008 in the Molt-4 T-ALL model.
Figure 4:
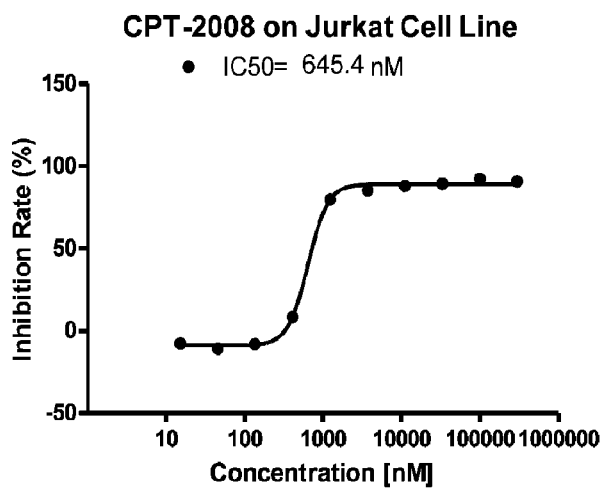
FIG. 4 shows the efficacy of CPT-2008 in the Jurkat T-cell leukemia model.
Figure 5:
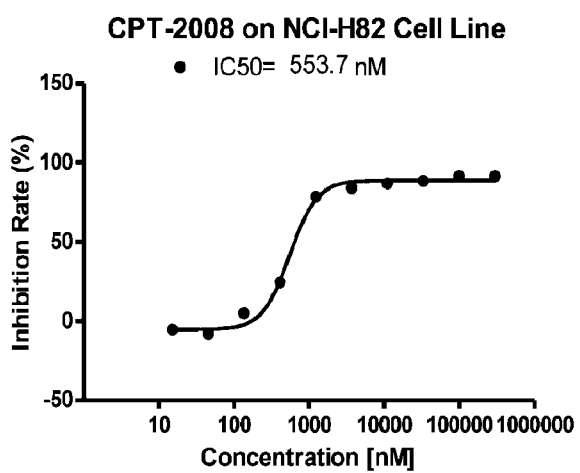
FIG. 5 shows the efficacy of CPT-2008 in the NCI-H82 SCLC model.
Figure 6:
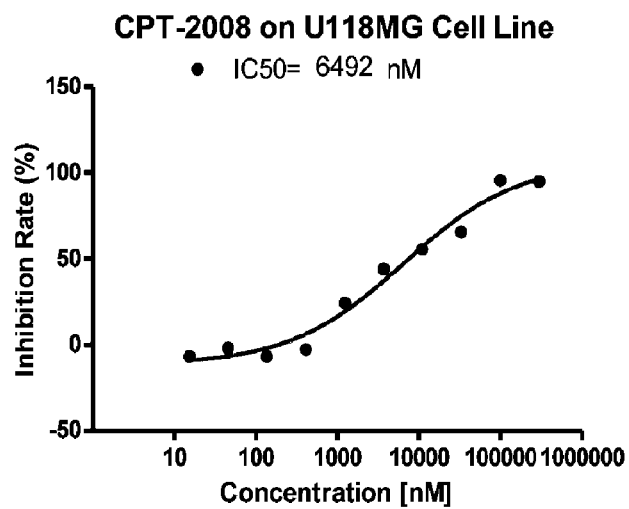
FIG. 6 shows the efficacy of CPT-2008 in the U118MG Glioblastoma model.
Figure 7:
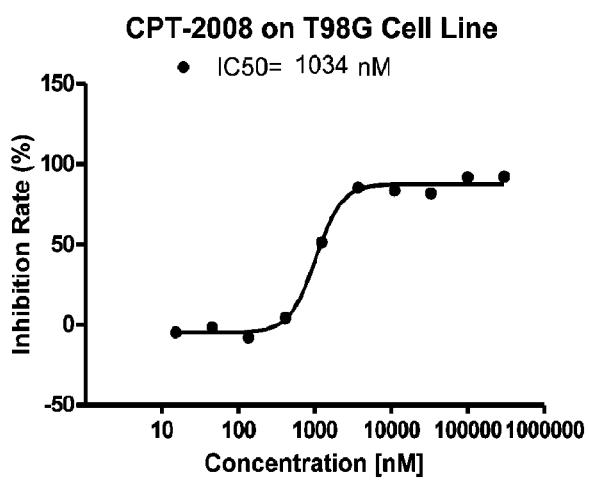
FIG. 7 shows the efficacy of CPT-2008 in the T98G Glioblastoma model.
Figure 8:
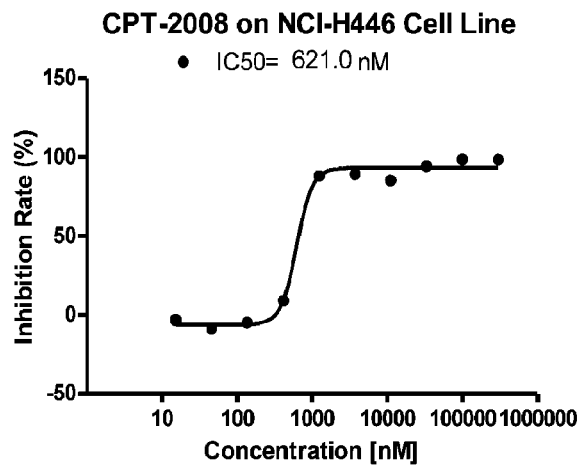
FIG. 8 shows the efficacy of CPT-2008 in the NCI-H446 SCLC model.
Figure 9:
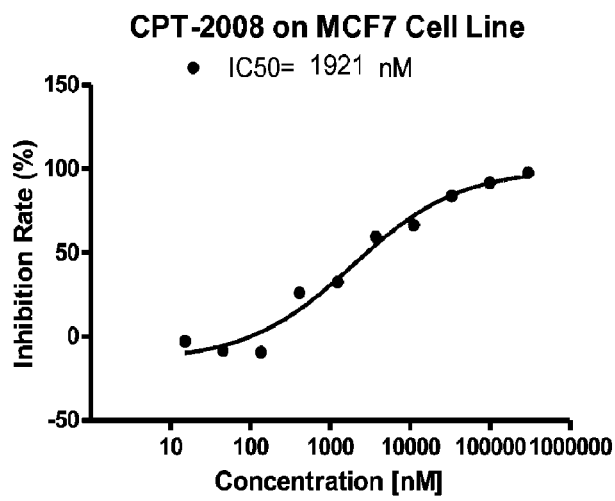
FIG. 9 shows the efficacy of CPT-2008 in the MCF7 breast cancer model.
Figure 10:
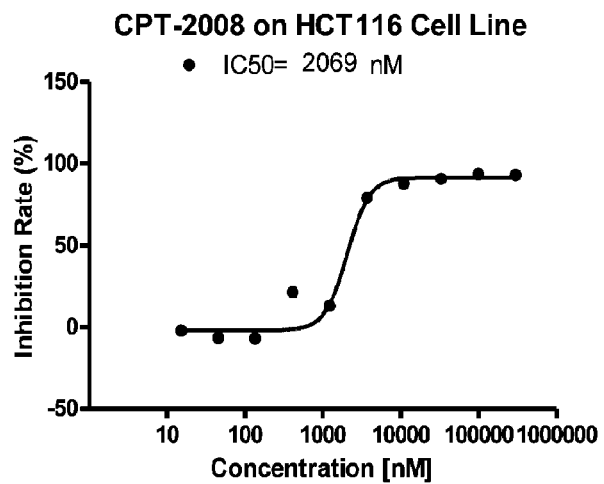
FIG. 10 shows the efficacy of CPT-2008 in the HCT-116 Colorectal cancer model.
Figure 11:
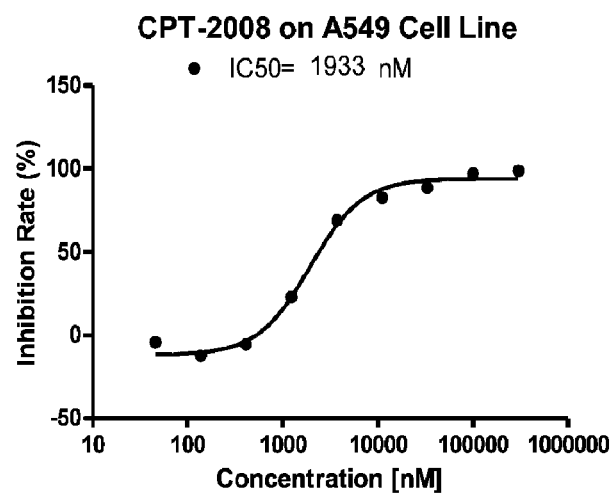
FIG. 11 shows the efficacy of CPT-2008 in the A549 NSCLC model.
Figure 12:
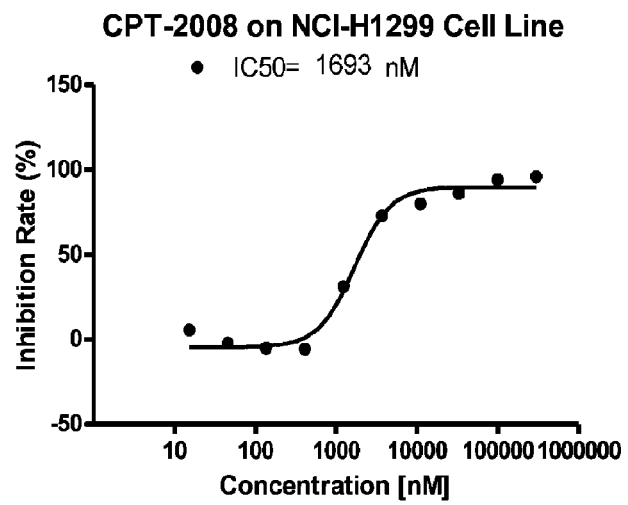
FIG. 12 shows the efficacy of CPT-2008 in the NCI-H1299 NSCLC model.
Figure 13:
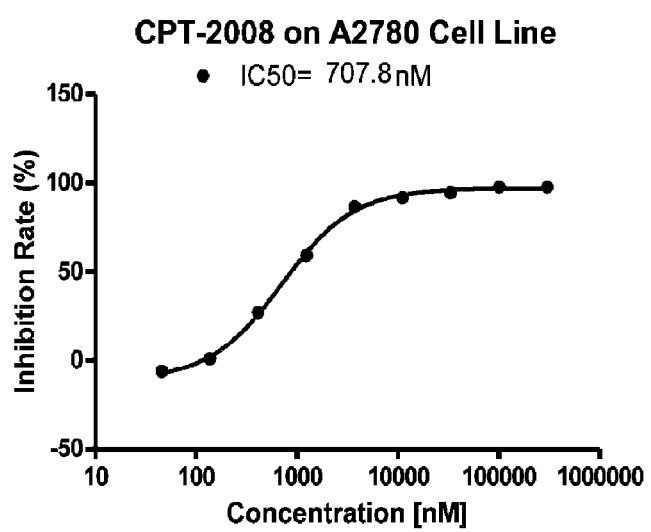
FIG. 13 shows the efficacy of CPT-2008 in the A2780 Ovarian cancer model.

The present invention pertains generally to compositions and methods of treating diseases associated with mitochondrial dysfunction. In particular, the invention relates to methods of treating cancer, neurodegenerative diseases (including Parkinson's disease, Alzheimer's disease, ALS, Huntington's disease), brain injuries (including Stroke, Seizures, Neuropathic pain, Traumatic brain injury, Spinal cord injury, Aneurysm, Subarachnoid hemorrhage), and certain non-neurological disorders (including Sepsis, Acute kidney injury, Cardiorenal syndrome, Cardiac Ischemia-reperfusion injury, Pulmonary arterial hypertension, Chronic obstructive pulmonary disease, vasoconstriction) using CPT-2008 or its derivatives to alter mitochondrial reactive oxygen species (ROS) generation, electron transport chain activity, mitochondrial morphology, or mitochondrial activity.

II. Definitions

As used herein, "CPT-2008" refers to 6-chloro-3-(2,4-dichloro-5-methoxyphenyl)-2-mercapto-7-methoxyquinazolin-4(3H)-one, i.e., a compound having the formula of $C_{16}H_{11}Cl_3N_2O_3S$ and a structure according to Formula I:

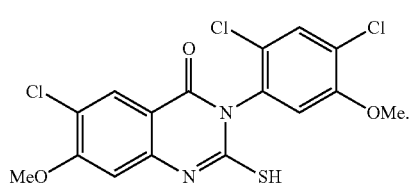

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to Alzheimer's disease) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

"Pharmaceutically acceptable excipient or carrier" refers to an excipient that may optionally be included in the compositions of the invention and that causes no significant adverse toxicological effects to the patient. "Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmitate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

As used herein, the terms "derivative" and "analog" refer to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

III. A New Pharmaceutical and Compositions Thereof

Provided herein are pharmaceutical compositions containing CPT-2008 and one or more pharmaceutically acceptable carriers or other excipients. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active ingredient in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing CPT-2008 can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Transdermal delivery of CPT-2008 can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, the pharmaceutical composition includes CPT-2008 and one or more additional active agents. In some embodiments, pharmaceutical compositions containing CPT-2008 and one or more additional active agents for treatment of neurological diseases are provided. Examples of such active agents include, but are not limited to, cholinesterase inhibitors (e.g., donepezil, donepezil/memantine, galantamine, rivastigmine, tacrine, or the like), alpha-7 nicotinic receptor modulators (e.g., alpha-7 agonists such as encenicline and APN1125), serotonin modulators (e.g., idalopirdine, RVT-101, citalopram, escitalopram, fluoxetine, fluvoxamine, paroxetine, sertraline, or the like), NMDA modulators (e.g., NMDA receptor antagonists such as memantine), Aβ-targeted therapies (e.g., pioglitazone, begacestat, atorvastatin, simvastatin, etazolate, tramiprosate, or the like), ApoE-targeted therapies (e.g., retinoid X receptor agonists), tau-targeted therapies (e.g., methylthioninium, leuco-methylthioninium, or the like), and anti-inflammatories (e.g., NSAIDs such as apazone, diclofenac, ibuprofen, indomethacin, ketoprofen, nabumetone, naproxen, piroxicam, or sulindac).

In some embodiments, pharmaceutical compositions containing CPT-2008 and one or more additional active agents for treatment of cancer are provided. Examples of such active agents include, but are not limited to, angiogenesis inhibitors (e.g., bevacizumab, ranibizumab, and the like), immune checkpoint inhibitors (e.g., a CTLA-4 antibody, an OX40 antibody, a PD-L1 antibody, a PD1 antibody, or a BY55 antibody), anthracyclines (e.g., doxorubicin, daunorubicin, and the like), platins (e.g., cisplatin, oxaliplatin, carboplatin, and the like), antimetabolites (e.g., 5-fluorouracil, methotrexate, and the like), kinase inhibitors (e.g., erlotinib, gefitinib, and the like), nucleoside analogs (e.g., gemcitabine, cytarabine, and the like), and taxanes (e.g., paclitaxel, docetaxel, and the like).

IV. Methods for the Treatment of Mitochondrial Diseases and Conditions

CPT-2008 and composition thereof are useful for treating diseases and conditions associated with mitochondrial dysfunction. Such diseases include, but are not limited to, cancer, neurodegenerative diseases, brain conditions, and non-neurological disorders.

In some embodiments, methods are provided wherein the disease or condition is a neurodegenerative disease. Examples of neurodegenerative diseases include, but are not limited to, Parkinson's disease, Alzheimer's disease, amyotrophic lateral sclerosis, and Huntington's disease.

In some embodiments, methods are provided wherein the disease or condition is a brain condition. Examples of brain conditions include, but are not limited to, stroke, seizure, neuropathic pain, traumatic brain injury, spinal cord injury, aneurysm, and subarachnoid hemorrhage.

In some embodiments, methods are provided wherein the disease or condition is a non-neurological disorder. Examples of non-neurological disorders include, but are not limited to, sepsis, acute kidney injury, cardiorenal syndrome, cardiac ischemia-reperfusion injury, pulmonary arterial hypertension, chronic obstructive pulmonary disease, and vasoconstriction. In some embodiments, the condition is human aging caused by mitochondrial dysfunction.

Also provided are methods and compositions for reducing cancer cell proliferation, e.g., in an individual having a cancer, e.g., so as to treat the cancer. By cancer it is meant the group of diseases involving unregulated cell growth. In cancer, cells proliferate, i.e., divide, uncontrollably, forming malignant tumors, and invading nearby parts of the body. The cancer may also metastasize, that is, spread to more distant parts of the body through the lymphatic system or bloodstream. The treatment may be prophylactic in terms of completely or partially preventing a cancer or symptom thereof and/or may be therapeutic in terms of a partial or complete cure for a cancer and/or adverse effect attributable to the cancer.

Treatment of cancer can include: (a) preventing the cancer from occurring in a subject which may be predisposed to the cancer but has not yet been diagnosed as having it; (b) inhibiting the cancer, i.e., arresting its development; or (c) relieving the cancer, i.e., causing regression of the cancer. The therapeutic agent may be administered before, during or after the onset of cancer. The treatment of ongoing cancer, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the cancer, and in some cases after the symptomatic stage of the cancer. The terms "individual," "subject," "host," and "patient," are used interchangeably herein and refer to any mammalian subject for whom diagnosis, treatment, or therapy is desired, particularly humans. In some instances, the subject methods and compositions reduce e.g., inhibit, the proliferation of the cancer. In some instances, the subject methods and compositions reduce, e.g., inhibit, the metastasis of the cancer.

In some embodiments, the cancer is a Notch-associated cancer; that is, the cancer is associated with, i.e., due at least in part to, active Notch signaling. By "Notch" it is meant the evolutionarily conserved single-pass transmembrane receptor that affects numerous cell fate decisions through short-range cell-cell interactions (Artavanis-Tsakonas and Muskavitch 2010). Notch protein (cLIN-12 and cGLP-1 in *C. elegans*, Notch in *Drosophila*, Notch1-4 in mammals) consists of an extracellular domain (NECD) with 29-36 epidermal growth factor (EGF) repeats for ligand binding, a transmembrane domain, and an intracellular domain (NICD) having transcriptional activity. By "active Notch signaling", it is meant that the Notch protein is active in the cancer cell, e.g., it is an activated Notch, or a constitutively active Notch, e.g., the Notch protein has been mutated such that the Notch protein or a domain thereof is always active. Examples of Notch-associated cancers include hematological malignancies, e.g., acute lymphoblastic leukemia (T-ALL); mammary gland tumors, e.g., breast cancer; brain tumors, e.g., glioblastoma multiforme (GBM); lung cancer; and intestinal cancer (Artavanis-Tsakonas and Muskavitch 2010). A cancer may be readily identified as a Notch-associated cancer by detecting in a cancerous cell, e.g., in a tumor biopsy or cell smear, a Notch mutation that results in constitutively active Notch. A number of mutations have been identified that result in constitutively active Notch signaling, which may be detected by, for example, chromosome spread or PCR as known in the art. Alternatively, a cancer may be identified as a Notch-associated cancer by detecting the upregulated activity of downstream effectors of Notch signaling, e.g., the upregulated activity of the non-canonical Notch signaling proteins e.g., elevated PINK1 expression, elevated mTORC2 signaling (increased Akt phosphorylation), and elevated respiratory chain complex assembly as compared to noncancerous cells.

Notch protein modulates cell activity by a canonical pathway and non-canonical pathways. In canonical Notch pathway signaling, Notch ligands (transmembrane proteins comprising three motifs: DSL (Delta, Serrate, LAG-2), DOS (Delta and OSM-11 like) and EGF repeats) bind to the EGF repeats of the Notch extracellular domain from adjacent cells. The ligand-Notch interaction allows members of the α-secretase/metalloprotease family (ADAM10/Kuzmanian, ADAM17/TACE) to cleave the extracellular domain of Notch, leading to sequential cytoplasmic cleavage of the intracellular domain of Notch by γ-secretase (a multi-subunit protease complex composed of presenilin (PS), nicastrin (NCT), Aph-1, Pen-2 and others). The freed intracellular domain translocates to the nucleus, where it interacts via its RAM domain with the DNA-binding transcription factor CSL ("CBF1/RBPjk" in vertebrates, "Suppressor of Hairless" in *Drosophila*, "Lag-1" in *C. elegans*) and acts as a co-activator for CSL, Mastermind-like proteins ("MAML1" in vertebrates, "Mastermind" in *drosophila*, "Lag-3" in *C. elegans*) and other cofactors such as CBP/p300 to transcriptionally activate Notch target genes (Kopan and Ilagan 2009). In the absence of free intracellular domain Notch, CSL functions as a sequence-specific repressor. Thus, genes that mediate canonical Notch signaling (that is, "canonical Notch signaling genes") would include genes encoding polypeptides of the γ-secretase complex, CSL ("CBF1/RBPjk" in vertebrates, "Suppressor of Hairless" in *Drosophila*, "Lag-1" in *C. elegans*), genes encoding Mastermind-like proteins ("MAML1" in vertebrates, "Mastermind" in *drosophila*, "Lag-3" in *C. elegans*) and the CBP/p300 gene.

Notch can also signal through non-canonical pathways. Non-canonical Notch signaling is CSL-independent and can be either ligand-dependent or independent (Kopan and Ilagan 2009). Although some genes are affected by non-canonical Notch function, in most cases the mediators of non-canonical Notch signaling are unknown. The most well studied and conserved effect of non-canonical Notch function is regulation of Wnt/β-catenin signaling. In this non-canonical Notch signaling pathway, Notch binds and titrate levels of the obligate Wnt-signaling component active β-catenin (Takebe et al. 2011). Therefore, active β-catenin activity may serve as a useful readout for non-canonical Notch signals. Other studied non-canonical Notch signaling pathways include signaling through NF-kappa B, signaling through the JNK pathway, and signaling through HES1 and MCK (Andersen et al. 2012).

Recently, mTORC2, Akt, and proteins that promote mitochondrial development or function, e.g., PINK1, mitochondrial respiratory chain complex proteins, mitochondrial fission proteins, and mitochondrial biogenesis proteins, are found to mediate non-canonical Notch signaling (Lee et al. 2013). For example, polypeptides of mitochondrial respiratory chain complex I (e.g., the 75 kD subunit, ND-75), the mitochondrial fission protein Dynamin-1-like protein (Drp1), and the mitochondrial biogenesis protein Peroxisome proliferator-activated receptor gamma coactivator 1-alpha (PGC-1α). Importantly, many of these genes in the non-canonical Notch signaling pathway encode proteins that are regulate mitochondrial function (Lee et al. 2013). As disclosed in the working examples, CPT-2008 is effective in targeting Notch-promoted cancer cell proliferation, e.g., proliferation of T-ALL (Molt-4, Jurkat cell lines) and glioblastoma (T98G, U118MG cell lines).

As an important regulator of neuronal development and function, Notch signaling is profoundly involved in many aspects of brain development, functioning, and maintenance. Deregulated Notch signaling has been implicated in the pathogenesis of brain tumor, stroke, neurodegeneration, neuropathic pain, traumatic brain injury, depression, and neuropsychiatric disorders (Mathieu et al., 2013; Zhang et al., 2018; Alfred and Vaccari, 2018). The fact that the outcome of Notch signaling is highly context-dependent suggests that non-canonical Notch function might be a norm rather than an exception. The fact that efficient inhibition of canonical Notch signaling has proved to be too toxic for clinical use, mostly due to unwanted on-target effects (Andersson and Lendahl, 2014), suggests that expanding methods for modulating Notch signaling beyond the canonical pathway will increase the available range of therapeutic options. It is thus expected that by inhibiting aberrant Notch activation through the non-canonical pathway, CPT-2008 will be of therapeutic value against a broad spectrum of brain diseases and conditions.

In some embodiments, methods for the treatment of T-acute lymphoblastic leukemia (T-ALL), small cell lung cancer (SCLC), non-small cell lung cancer (NSCL), glioblastoma, colorectal cancer, breast cancer, and/or ovarian cancer are provided.

CPT-2008 can be administered at any suitable dose in the methods provided herein. In general, CPT-2008 will be administered at a dose ranging from about 0.1 milligrams to about 1000 milligrams per kilogram of a subject's body weight (i.e., about 0.1-1000 mg/kg). The dose of the CPT-2008 can be, for example, about 0.1-1000 mg/kg, or about 1-500 mg/kg, or about 25-250 mg/kg, or about 50-125 mg/kg. The dose of the CPT-2008 can be about 0.1-1 mg/kg, or about 1-50 mg/kg, or about 50-100 mg/kg, or about 100-150 mg/kg, or about 150-200 mg/kg, or about 200-250 mg/kg, or about 250-300 mg/kg, or about 350-400 mg/kg, or about 450-500 mg/kg, or about 500-550 mg/kg, or about 550-600 mg/kg, or about 600-650 mg/kg, or about 650-700 mg/kg, or about 700-750 mg/kg, or about 750-800 mg/kg, or about 800-850 mg/kg, or about 850-900 mg/kg, or about 900-950 mg/kg, or about 950-1000 mg/kg. The dose of the CPT-2008 can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. CPT-2008 can be administered, orally, topically, parenterally, intravenously, intraperitoneally, intramuscularly, intralesionally, intranasally, subcutaneously, or intrathecally using a suitable vehicle, including any of the compositions described above. Alternatively, the CPT-2008 can be administered via a suppository or via implantation of a slow-release device, e.g., a mini-osmotic pump.

The dosages can be varied depending upon the requirements of the patient, the severity of disease or condition being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the disease or condition.

Administration of CPT-2008 can be conducted for a period of time which will vary depending upon the nature of the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage of CPT-2008 can either be increased in the event the patient does not respond significantly to a particular dosage level, or the dose can be decreased if an alleviation of the symptoms is observed, or if unacceptable side effects are seen with a particular dosage. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be conducted, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the symptoms go into remission or generally improves, the dosage may be maintained or kept at lower than maximum amount. If the condition or symptoms worsen, the first dosage regimen can be resumed until an improvement is seen, and the second dosing regimen can be implemented again. This cycle can be repeated multiple times as necessary.

V. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Synthesis of CPT-2008

A convergent synthetic approach was taken to make CPT-2008, in which two fragments (compound 3 and compound 5) were made separately and combined to make the final product (FIG. 1) as described below. The final product had the formula of $C_{16}H_{11}Cl_3N_2O_3S$, a molecular weight of 417.69 g/mole, and a purity greater than 95% as determined by HPLC and LCMS/$^1$H NMR.

The chemical synthesis of CPT-2008 involved the following steps.

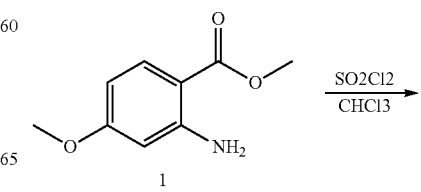

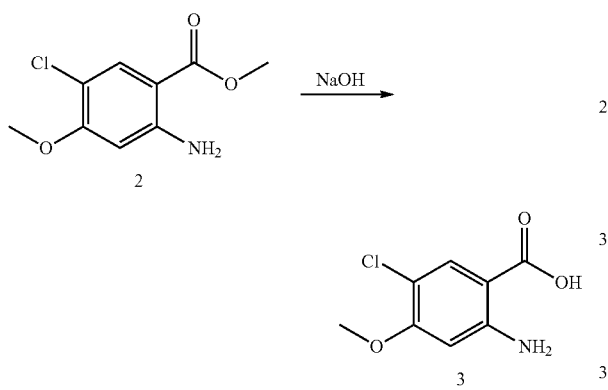

Preparation of compound 2. To a solution of compound 1 (50 g, 276 mmol) in CHCl$_3$ (600 mL) was added SO$_2$Cl$_2$ (26 mL, 331 mmol) in an ice bath and stirred at reflux for 4 hours. The reaction mixture was concentrated to afford the crude product, which was purified by trituration with PE/EA=1:1 (200 mL) to get desired product as white solid (36 g, 61% yield). $^1$H NMR (400 MHz, DMSO-d6) δ 7.64 (1H, s), 6.48 (1H, s), 3.81 (3H, s), 3.75 (3H, s).

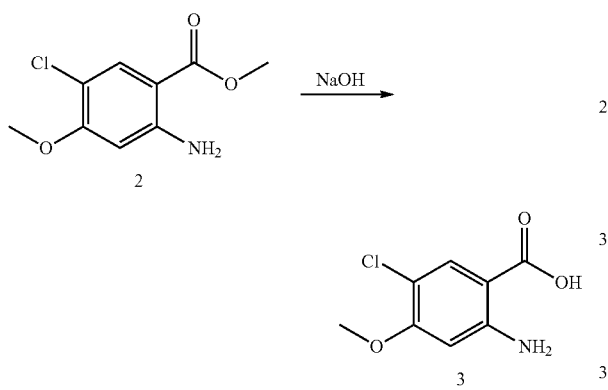

Preparation of compound 3. A mixture of compound 2 (26 g, 167 mmol) in a solution of NaOH (13.4 g, 0.334 mmol) in water (400 mL) was stirred at r.t. overnight, after which time complete reaction was observed by TLC. The reaction was acidified with 2N HCl and filtered, washed with water, and dried to provide the desired product as a white solid (30 g, 90% yield). $^1$H NMR (400 MHz, DMSO-d6) δ 7.62 (1H, s), 6.44 (1H, s), 3.80 (3H, s).

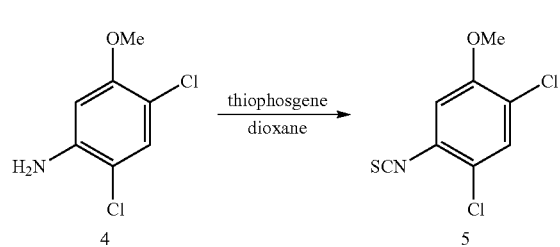

Preparation of compound 5. To a solution of compound 4 (28.7 g, 149 mmol) in dioxane (300 mL) was added thiophosgene (19.5 mL, 253 mmol), and the mixture was stirred at reflux for 2 h. Complete reaction was observed by TLC, and the reaction mixture was concentrated to afford the crude product as a yellow solid (35 g, 100% yield). $^1$H NMR (400 MHz, CDCl3) δ 7.41 (1H, s), 6.76 (1H, s), 3.88 (3H, s).

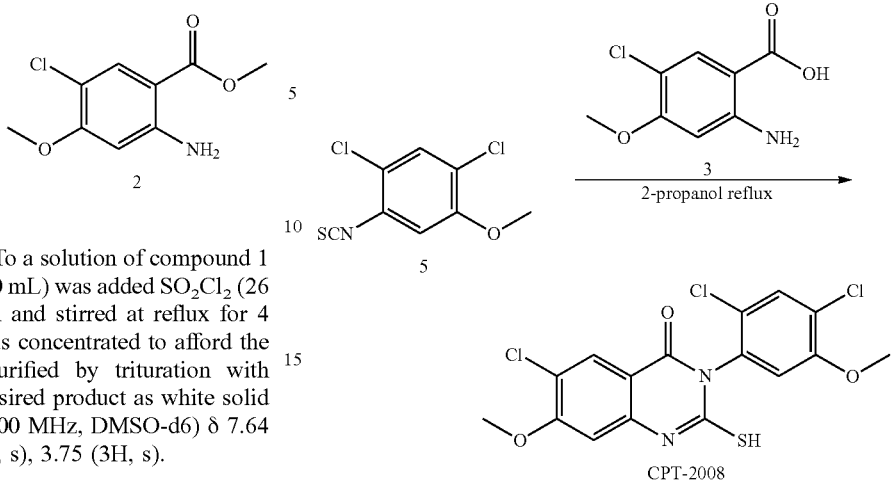

Preparation of CPT-2008. To a mixture of compound 5 (35 g, 149 mmol) and compound 3 (30 g, 149 mmol) in 2-propanol (500 mL) was added NaOMe (402 mg, 7.4 mmol), and the mixture was stirred overnight at reflux. The reaction was concentrated, and the resulting residue was suspended in DCM (200 mL) and filtered. The filter cake was washed with DCM (50 mL) to obtain the product as a white solid (21.5 g, 34% yield over two steps). $^1$H NMR (400 MHz, DMSO-d6) δ 13.21 (1H, s), 7.93 (1H, s), 7.79 (1H, s), 7.43 (1H, s), 7.12 (1H, s), 3.98 (3H, s), 3.82 (3H, s); ESI LC-MS: R$_f$=1.730 min, 418.8 [M+1]$^+$.

Example 2: Anti-Tumor Activity of CPT-2008 in Cell Culture (a) Reagents and Materials CellTiter-Glo Luminescent Cell Viability Assay Kit was obtained from Promega. RPMI 1640 was obtained from Invitrogen. Fetal Bovine Serum (FBS) was obtained from Corning. L-glutamine was obtained from Invitrogen. 100× Penicillin-Streptomycin was obtained from HyClone. 0.05% Trypsin-EDTA (T-E) was obtained from Invitrogen. DPBS was obtained from Corning. DMSO was obtained from Sigma. Black 384 well plate was obtained from Greiner. 96-well V bottom plate was obtained from Axygen.

(b) Experimental Procedure

Cell seeding (Day "−1"): The cell density of eight adherent cell lines was adjusted according to supplier-recommended information. 50 μL cells were seeded in four 384-well-plates, and 50 μL DPBS was added to the edge wells.

Compound preparation (Day 0): All test compounds were dissolved in DMSO and stored in a nitrogen cabinet. The stock concentration of the test compounds was 120 mM. The stock concentration of the reference compounds was 10 mM. The reference compound paclitaxel was diluted with DMSO to provide a 400 μM stock solution.

Cell treatment with test compounds (Day 0): Test compounds (125 nL in DMSO) were added to the wells using an ECHO liquid handling system (Labcyte Inc.) and serially diluted by three fold, providing 10 doses in each series with a maximum concentration of 300 μM. Equal volumes of DMSO without test compound were transferred to control rows in the well plate.

Cell seeding (Day 0): The cell density of two suspension cell lines was adjusted according to supplier-recommended information. 50 μL of cells were seeded in a 384-well-plate. 50 μL of DPBS were added to the edge wells.

Using the procedures described above, the highest concentration for the reference compound paclitaxel was 1 μM and the DMSO concentration across the well plate was 0.25% (v/v).

Assay (Day 3): After the cells were treated with the compounds for 72 hours, the plates were equilibrated at room temperature for approximately 30 minutes. 25 μL of CellTiter Glo reagent was added to each well, and the luminescence in each well was measured after 10 min using an ENVISION fluorescence plate reader (PerkinElmer).

(c) Data Analysis Method

Calculation formula: Inhibition %=(Max−Sample Value)/Max*100.

Curves were fitted by Prism with a Sigmoidal dose-response (variable slope) model and generated by 4 Parameter Logistic Model or Sigmoidal Dose-Response Model, $Y=Bottom+(Top-Bottom)/(1+10^{((log EC50-x)*Hill Slope)})$.

(d) Results

CPT-2008 exhibits potent anti-tumor activity in multiple cellular models of cancer. To evaluate the anti-tumor activity of CPT-2008, the growth inhibitory effect of the compound was measured in various human cancer cell lines after 72 hour incubation. In the assays, all the cell lines met the criteria that the viability of adherent/mixed cells was greater than 90% and the viability of suspension cells was greater than 85% during the initial cell plating. All the cell plates in this assay met the criteria that coefficient of variation (CV) <10%. The data recorded for the paclitaxel reference compound were consistent with the historical published data.

The cell lines included the following cancer models: T-ALL (T-acute lymphoblastic leukemia) model (Molt-4), T cell leukemia (Jurkat), small cell lung cancer (SCLC: NCH-H82 and NCI-H446), non-small cell lung cancer (NSCLC: NCI-H1299 and A549), glioblastoma (T98G and U118MG), breast cancer (MCF7), ovarian cancer (A2780), and colorectal cancer (HCT116). CPT-2008 exhibited IC50s in the nM range in the NCI-H82, NCI-H446, Jurkat, and A2780 cancer cell lines. In the other cell lines, it exhibited IC50s in the low μM range. These results indicate that CPT-2008 possesses potent anti-tumor activity in human cell culture models of cancer.

Figure 14:
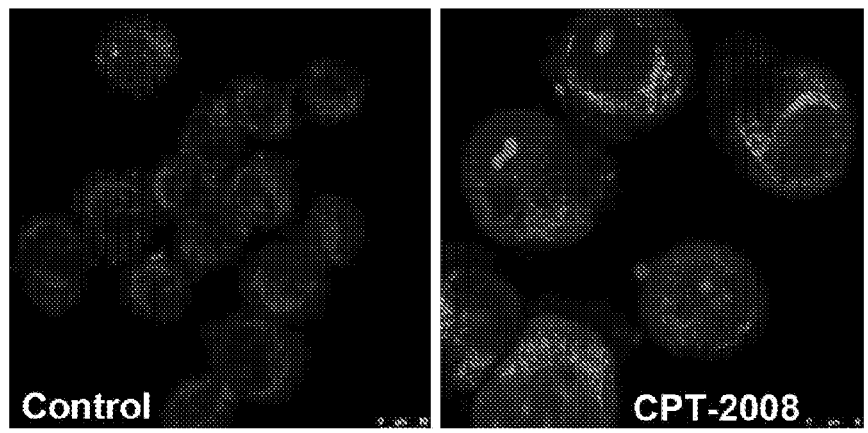
FIG. 14 shows the effect of CPT-2008 on mitochondrial calcium in human GBM cells. GBM cells treated with DMSO vehicle (control) or with CPT-2008 in DMSO were stained with Rhod-2AM to probe mitochondrial calcium (mito-$Ca^{2+}$) level. CPT-2008 elevated mito-$Ca^{2+}$.
Figure 15:
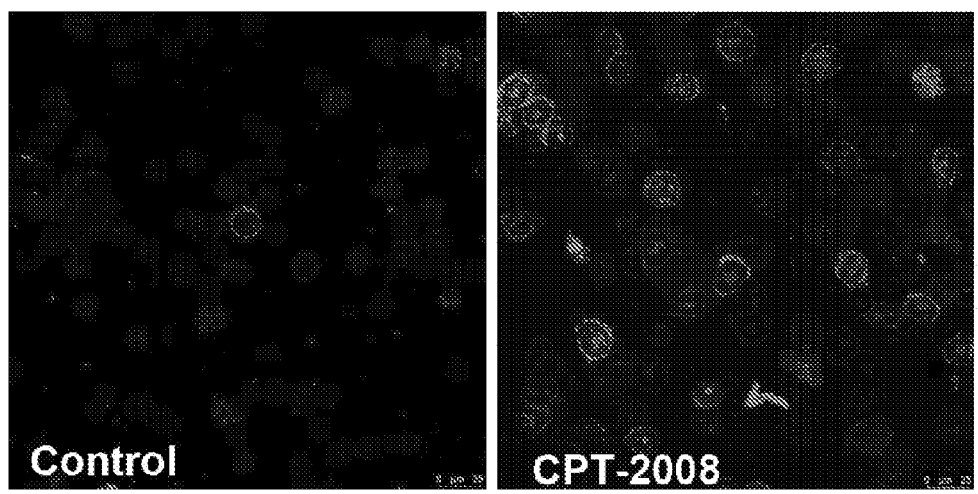
FIG. 15 shows the effect of CPT-2008 on mitochondrial ROS in human GBM cells. GBM cells treated with DMSO vehicle (control) or with CPT-2008 in DMSO were stained with Mito-SOX to probe mitochondrial ROS level. CPT-2008 significantly elevated mitochondrial ROS level.
Figure 16:
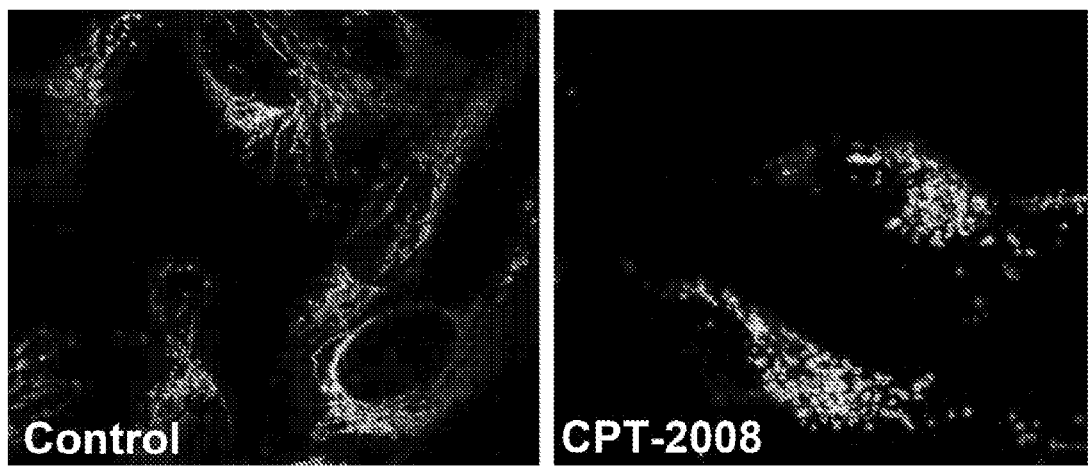
FIG. 16 shows the effect of CPT-2008 on mitochondrial morphology in GBM cells. GBM cells treated with DMSO (control) or CPT-2008 in DMSO were immunostained for TOM-20 to reveal mitochondrial morphology. Note that CPT-2008 induced mitochondrial size reduction.
Figure 17:
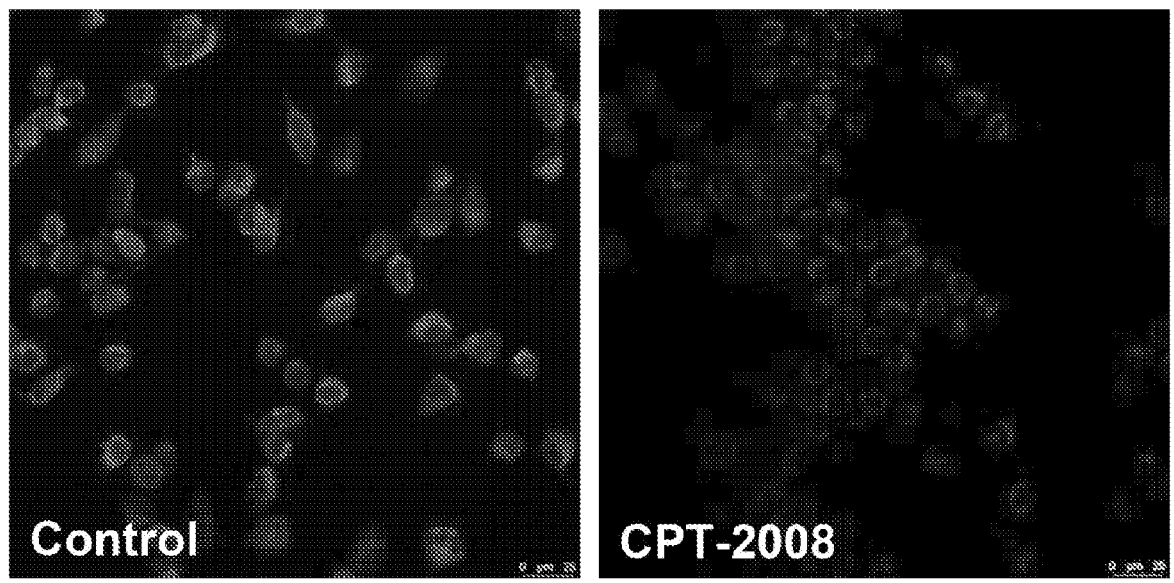
FIG. 17 shows the effect of CPT-2008 on mitochondrial membrane potential in human GBM cells. GBM cells treated with DMSO vehicle or with CPT-2008 in DMSO were stained with TMRM to probe mitochondrial membrane potential. CPT-2008 dramatically reduced mitochondrial membrane potential.
Figure 18:
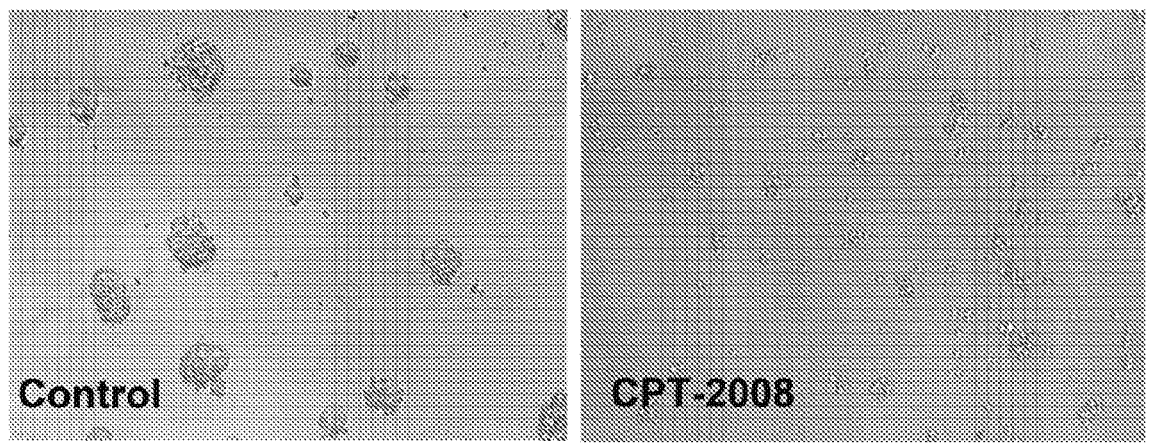
FIG. 18 shows the effect of CPT-2008 in inhibiting the self-renewal of human GBM cells. Control: cells treated with DMSO vehicle; CPT-2008: cells treated with 20 uM CPT-2008. Note that while DMSO treated GBM cells formed neurospheres indicating of cancer stem cell self-renewal, CPT-2008 treated cells lost such ability.

CPT-2008 affects mitochondrial function. The efficacy of CPT-2008 against a broad range of cancer models suggest that its mechanism of action is unique, targeting a general cellular mechanism required for cancer cell proliferation. Given the important role of mitochondria in maintaining cancer cells, especially cancer stem cells, the effects of CPT-2008 on a number of mitochondrial parameters in human glioblastoma (GBM) cells were texted next. First, the effects of CPT-2008 on mitochondrial ROS level were studied. For this purpose, the mito-SOX dye was used. Mito-SOX can specifically monitor mitochondrial ROS levels. As shown in FIG. 15, CPT-2008 caused significant increase of mitochondrial ROS in GBM cells. The effect of CPT-2008 on mitochondrial membrane potential, a key factor that determines mitochondrial health and activity, was also measured using the TRM dye. As shown in FIG. 17, CPT-2008 induced a dramatic reduction of mitochondrial membrane potential in GBM cells. The effect of CPT-2008 on mitochondrial calcium homeostasis was also measured using the Rhod-2AM dye, which specifically monitors mitochondrial calcium levels. As shown in FIG. 14, CPT-2008 caused an increase of mitochondrial calcium. The effect of CPT-2008 on mitochondrial morphology was also measured using immunostaining of the mitochondrial outer membrane marker Tom20. As shown in FIG. 16, CPT-2008 induced a dramatic fragmentation of mitochondria, resulting in small and round mitochondria as opposed to the long and tubular mitochondria in control cells. Together, these results indicate that CPT-2008 affects mitochondrial function. Finally, the effect of CPT-2008 on the self-renewal of GBM cells was tested. As shown in FIG. 18, CPT-2008 significantly inhibited the self-renewal of GBM cells, as measured by the ability to form neurospheres in culture.

Figure 19A:
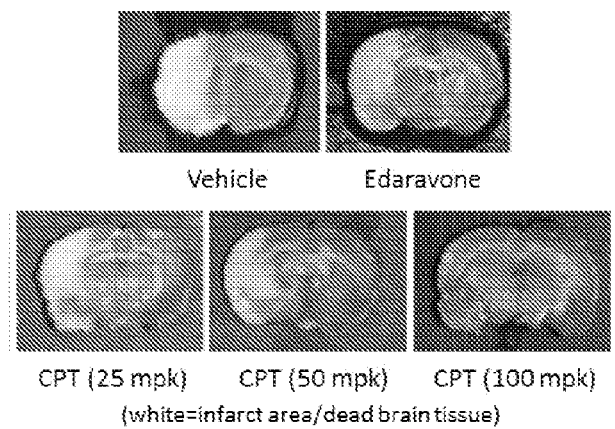
FIG. 19A shows the level of brain tissue infarction in rats treated with vehicle or edaravone (top panels) and rats treated with CPT-2008 (bottom panels).
Figure 19B:
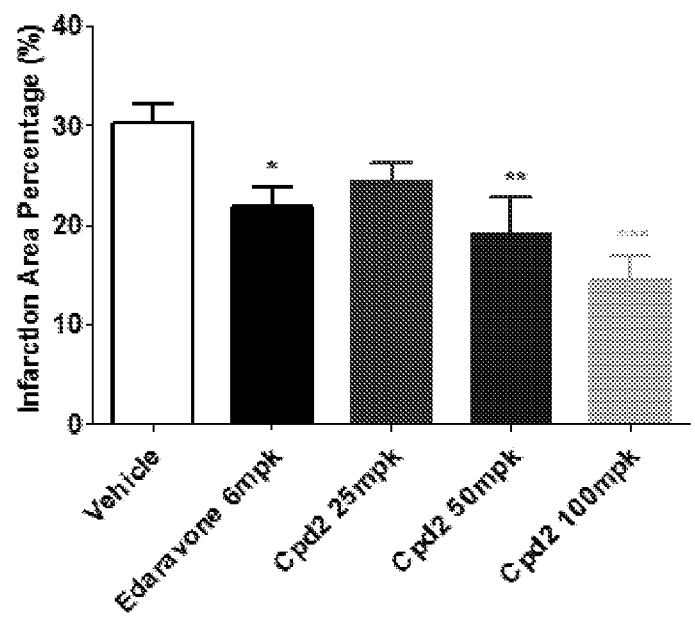
FIG. 19B shows the brain tissue infarction area for rats treated with edaravone or CPT-2008. *$P<0.05$, $P<0.01$, *$P<0.001$ vs. vehicle, by one-way ANOVA post Dunnett's test.

Example 3: CPT-2008 Provides Improved Protective Effects in an In Vivo Stroke Model Edaravone (3-methyl-1-phenyl-2-pyrazolin-5-one) is a reactive oxygen species (ROS) scavenger approved for the treatment of stroke and ALS in Japan, and for the treatment of ALS in the United States. The efficacy of CPT-2008 for preventing brain damage in a rat middle cerebral artery occlusion (MCOA) model was compared with the efficacy of edaravone. Sprague-Dawley rats were dosed with vehicle, edaravone (6 mg/kg), or CPT-2008 (25-100 mg/kg), and the level of infarcted brain tissue was assessed. In this study rats underwent middle cerebral artery occlusion (MCAO) for 1.5 h followed by 24 h reperfusion. CPT-2008 was given intraperitoneally 0 h and 8 h after reperfusion, and behavior deficits and brain insult were assessed by Longa score scale and TTC staining, respectively. As shown in FIG. 19A and FIG. 19B, the reduced levels of dead brain tissue upon treatment with CPT-2008 indicate that CPT-2008 outperforms edaravone. It is believed that the improved benefit of CPT-2008 is due, in part, to prevention ROS formation in brain tissue mitochondria.

Example 4: CPT-2008 Exhibits Efficacy in a Chemo-Induced Neuropathic Pain Model

Figure 20:
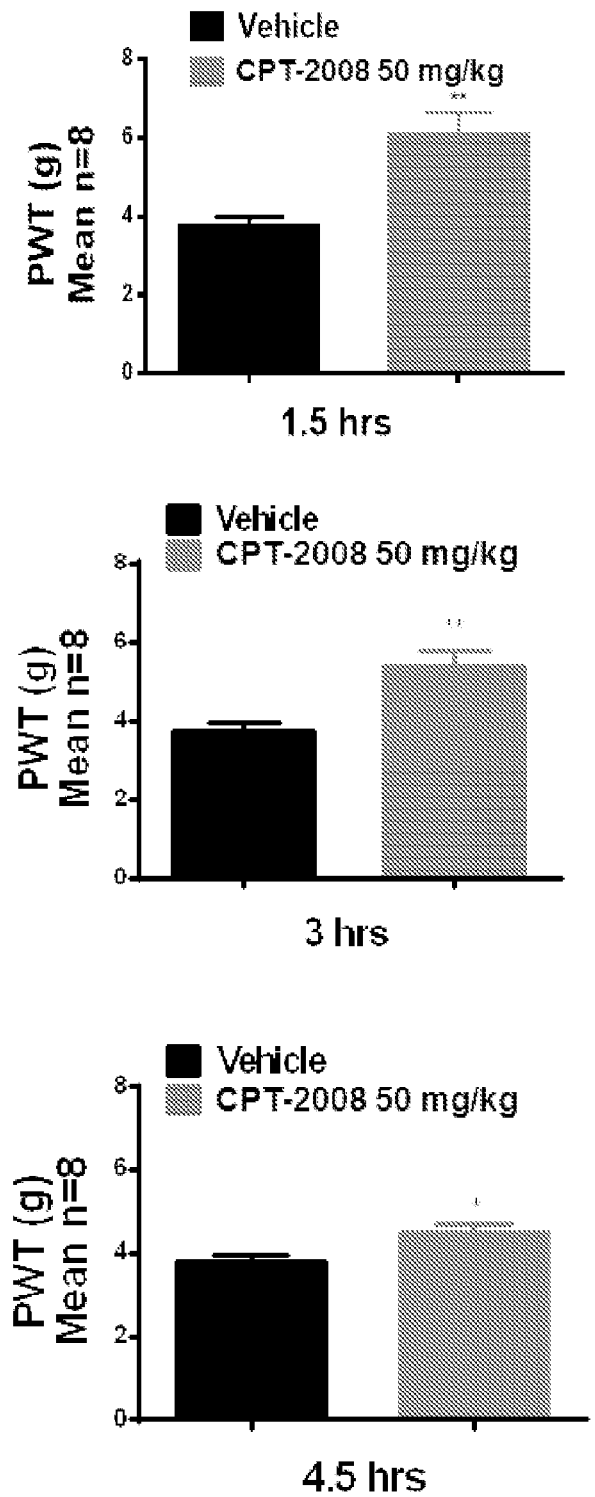
FIG. 20 shows paw withdrawal threshold (PWT) measurements in paclitaxel-treated mice following administration of CPT-2008. *$p<0.05$, **$p<0.01$ vs. vehicle group by unpaired t test.

An estimated 30-40% of cancer patients undergoing chemotherapy experience peripheral neuropathic pain, a neuroinflammation-induced debilitating side effect that causes patients to stop their treatment early or take lower doses. The effects of CPT-2008 in reducing neuropathic pain were studied in paclitaxel-treated rats. After paclitaxel treatment for 8 days, Sprague-Dawley rats were housed for additional days. On day 22, 16 rats were randomly separated into two groups. One group was dosed with vehicle, and the other group was dosed via intraperitoneal injection with CPT-2008 at 100 mg/kg. Pain (mechanical allodynia) test subjects was assessed using a paw withdrawal test (PWT) as described by Xie ("Activation of notch signaling mediates the induction and maintenance of mechanical allodynia in a rat model of neuropathic pain." Molecular Medicine Reports 12: 639-644, 2015). Rats were measured for paw withdrawal threshold post dosing of test compound at 1.5 h, 3 h, and 4.5 h. Administration of CPT-2008 to paclitaxel-treated animals decreased pain sensitivity, as indicated by the increased threshold values shown in FIG. 20.

Example 5: Study of CPT-2008 Pharmacokinetic Properties

Sprague-Dawley rats were administered CPT-2008 by IV or PO. Blood samples (about 1 mL) were collected via cardiac puncture after euthanasia by carbon dioxide inhalation at 5 min, 15 min, 30 min, 1 h, 2 h, 4 h, 8 h, 24 h of post dose. Blood samples were placed into tubes containing heparin sodium and centrifuged at 3500 rpm for 10 minutes at 4° C. to separate plasma from the samples. Following centrifugation, the resulting plasma was transferred to labeled tubes and stored frozen at −80° C. pending bioanalysis. The brain each studied animal at each time point was collected after the animal was euthanized by carbon dioxide inhalation. The whole tissue was harvested, excised and then placed into one tube per tissue per animal. The tissue samples were placed on dry ice and then stored at −80° C. until bioanalysis.

Figure 21A:
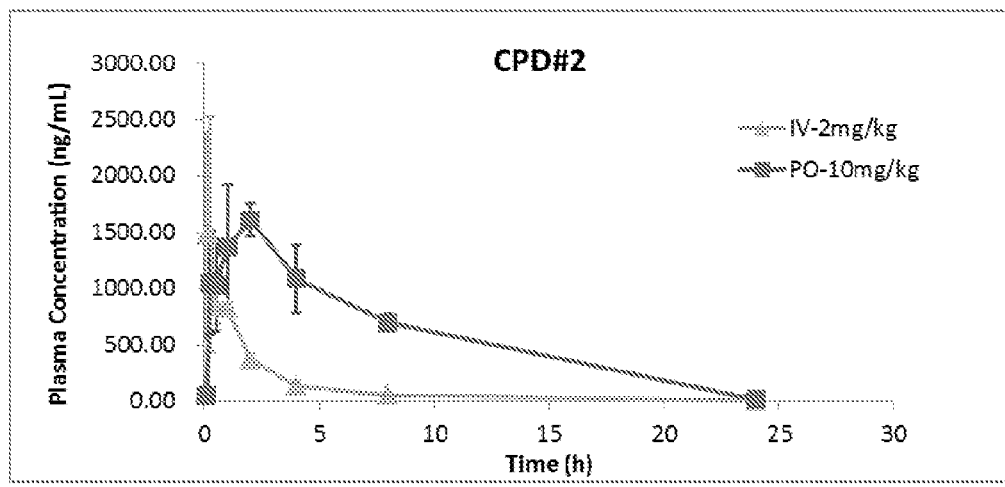
FIG. 21A shows the CPT-2008 plasma concentration following oral administration and intravenous administration to Sprague-Dawley rats.
Figure 21B:
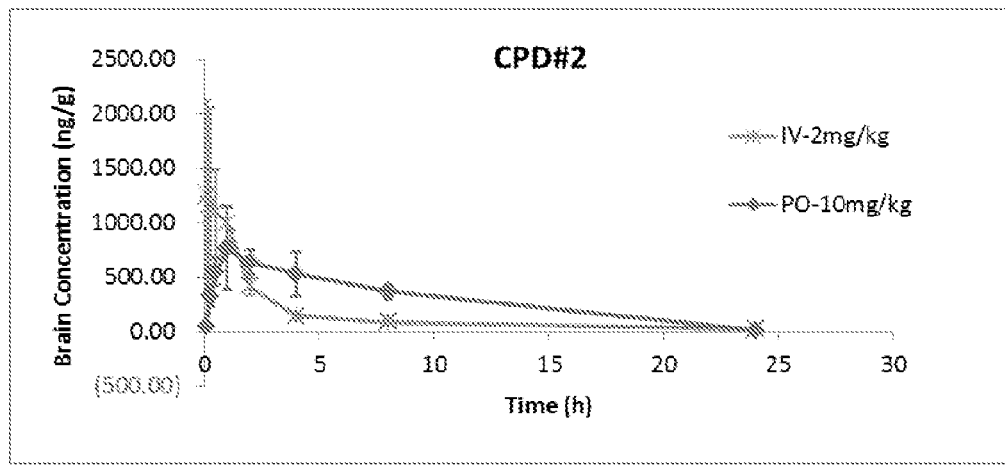
FIG. 21B shows the CPT-2008 brain concentration following oral administration and intravenous administration to Sprague-Dawley rats.

CPT-2008 was found to efficiently cross the blood brain barrier, as shown in FIG. 21A and FIG. 21B. The measured plasma bioavailability for CPT-2008 in rats was 94.5%.

The measured brain bioavailability was 38.97%, with drug detected in brain plasma, cerebrum, cerebellum, and brain stem. In beagle dogs, the concentration of CPT-2008 in various brain regions (left cerebrum, right cerebrum, cerebellum, and brain stem) reached 1.5 to 2 µM, which was close to or above the compound's $EC_{50}$ values in a number of cancer cell lines. The compound also exhibited excellent stability in microsomes and hepatocytes. For example, the measured half-life was around 3.6 hours in human microsomes and around 94.3 hours (3.9 days) in human hepatocytes.

VI. References

Alfred V, Vaccari T. 2018. "Mechanisms of Non-canonical Signaling in Health and Disease: Diversity to Take Therapy up a Notch?" *Adv Exp Med Biol.* 1066:187-204. \

Andersen P, Uosaki H, Shenje L T, Kwon C. 2012. "Non-canonical Notch signaling: emerging role and mechanism." *Trends Cell Biol* 22: 257-265.

Andersson E R, Lendahl U. 2014. "Therapeutic modulation of Notch signalling—are we there yet?" *Nat Rev Drug Discov.* 13 (5): 357-78.

Areti A, Yerra V G, Komirishetty P, Kumar A. 2016. "Potential Therapeutic Benefits of Maintaining Mitochondrial Health in Peripheral Neuropathies." *Curr Neuropharmacol* 14: 593-609

Artavanis-Tsakonas S, Muskavitch M A. 2010. "Notch: the past, the present, and the future." *Curr Top Dev Biol* 92: 1-29.

Arun S, Liu L, Donmez G. 2016. "Mitochondrial Biology and Neurological Diseases." *Curr Neuropharmacol* 14: 143-154.

Cahill J, Calvert J W, Zhang J H. 2006. "Mechanisms of early brain injury after subarachnoid hemorrhage." *J Cereb Blood Flow Metab* 26: 1341-1353.

Dawson T M, Dawson V L. 2017. "Mitochondrial Mechanisms of Neuronal Cell Death: Potential Therapeutics." *Annu Rev Pharmacol Toxicol* 57: 437-454.

de Moura M B, dos Santos L S, Van Houten B. 2010. "Mitochondrial dysfunction in neurodegenerative diseases and cancer." *Environ Mol Mutagen* 51: 391-405.

Emma F, Montini G, Parikh S M, Salviati L. 2016. "Mitochondrial dysfunction in inherited renal disease and acute kidney injury." *Nat Rev Nephrol* 12: 267-280.

Galluzzi L, Kepp O, Kroemer G. 2016. "Mitochondrial regulation of cell death: a phylogenetically conserved control." *Microb Cell* 3: 101-108.

Ganguly G, Chakrabarti S, Chatterjee U, Saso L. 2017. "Proteinopathy, oxidative stress and mitochondrial dysfunction: cross talk in Alzheimer's disease and Parkinson's disease." *Drug Des Devel Ther* 11: 797-810.

Glancy B, Balaban R S. 2012. "Role of mitochondrial $Ca^{2+}$ in the regulation of cellular energetics." *Biochemistry* 51: 2959-2973.

Hedskog L, Zhang S, Ankarcrona M. 2012. "Strategic role for mitochondria in Alzheimer's disease and cancer." *Antioxid Redox Signal* 16: 1476-1491.

Hiebert J B, Shen Q, Thimmesch A R, Pierce J D. 2015. "Traumatic brain injury and mitochondrial dysfunction." *Am J Med Sci* 350: 132-138.

Kauppila T E S, Kauppila J H K, Larsson N G. 2017. "Mammalian Mitochondria and Aging: An Update." *Cell Metab* 25: 57-71.

Kopan R, Ilagan M X. 2009. "The canonical Notch signaling pathway: unfolding the activation mechanism." *Cell* 137: 216-233.

Lee K S, Wu Z, Song Y, Mitra S S, Feroze A H, Cheshier S H, Lu B. 2013. "Roles of PINK1, mTORC2, and mitochondria in preserving brain tumor-forming stem cells in a noncanonical Notch signaling pathway." *Genes & development* 27: 2642-2647.

Lerner C A, Sundar I K, Rahman I. 2016. "Mitochondrial redox system, dynamics, and dysfunction in lung inflammaging and COPD." *Int J Biochem Cell Biol* 81: 294-306.

Lesnefsky E J, Chen Q, Tandler B, Hoppel C L. 2017. "Mitochondrial Dysfunction and Myocardial Ischemia-Reperfusion: Implications for Novel Therapies." *Annu Rev Pharmacol Toxicol* 57: 535-565.

Lleonart M, Grodzicki R, Graifer D, Lyakhovich A. 2017. "Mitochondrial dysfunction and potential anticancer therapy." *Med Res Rev.*

Malhotra J D, Kaufman R J. 2011. "ER stress and its functional link to mitochondria: role in cell survival and death." *Cold Spring Harbor perspectives in biology* 3: a004424.

Mathieu P, Adami P V, Morelli L. 2013. "Notch signaling in the pathologic adult brain." *Biomol Concepts.* 4 (5):465-76.

Paillusson S, Stoica R, Gomez-Suaga P, Lau D H, Mueller S, Miller T, Miller C C. 2016. "There's Something Wrong with my MAM; the ER-Mitochondria Axis and Neurodegenerative Diseases." *Trends Neurosci* 39: 146-157.

Perumalsamy L R, Nagala M, Sarin A. 2010. "Notch-activated signaling cascade interacts with mitochondrial remodeling proteins to regulate cell survival." *Proceedings of the National Academy of Sciences of the United States of America* 107: 6882-6887.

Pickrell A M, Youle R J. 2015. "The roles of PINK1, parkin, and mitochondrial fidelity in Parkinson's disease." *Neuron* 85: 257-273.

Pieczenik S R, Neustadt J. 2007. "Mitochondrial dysfunction and molecular pathways of disease." *Exp Mol Pathol* 83: 84-92.

Ratliff B B, Abdulmandi W, Pawar R, Wolin M S. 2016. "Oxidant Mechanisms in Renal Injury and Disease." *Antioxid Redox Signal* 25: 119-146.

Rugarli E I, Langer T. 2012. "Mitochondrial quality control: a matter of life and death for neurons." *The EMBO journal.*

Stepien K M, Heaton R, Rankin S, Murphy A, Bentley J, Sexton D, Hargreaves I P. 2017. "Evidence of Oxidative Stress and Secondary Mitochondrial Dysfunction in Metabolic and Non-Metabolic Disorders." *J Clin Med* 6.

Sui B D, Xu T Q, Liu J W, Wei W, Zheng C X, Guo B L, Wang Y Y, Yang Y L. 2013. "Understanding the role of mitochondria in the pathogenesis of chronic pain." *Postgrad Med J* 89: 709-714.

Sutendra G, Michelakis E D. 2014. "The metabolic basis of pulmonary arterial hypertension." *Cell Metab* 19: 558-573.

Takebe N, Harris P J, Warren R Q, Ivy S P. 2011. "Targeting cancer stem cells by inhibiting Wnt, Notch, and Hedgehog pathways." *Nat Rev Clin Oncol* 8: 97-106.

Wallace D C. 2005. "A mitochondrial paradigm of metabolic and degenerative diseases, aging, and cancer: a dawn for evolutionary medicine." *Annu Rev Genet* 39: 359-407.

Wallace D C. 2012. "Mitochondria and cancer." *Nat Rev Cancer* 12: 685-698.

Zhang R, Engler A, Taylor V. 2018. "Notch: an interactive player in neurogenesis and disease." *Cell Tissue Res.* 371 (1):73-89

Zsurka G, Kunz W S. 2015. "Mitochondrial dysfunction and seizures: the neuronal energy crisis." *Lancet Neurol* 14: 956-966.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound according to Formula I:

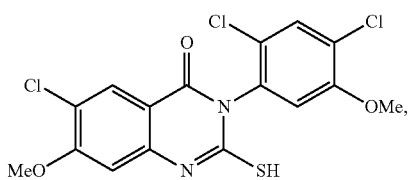

or a pharmaceutically acceptable salt thereof.

2. A pharmaceutical composition for treating a disease or condition associated with mitochondrial dysfunction, the composition comprising the compound of claim 1 according to Formula I, a pharmaceutically acceptable salt thereof, or a derivative thereof, and a pharmaceutically acceptable carrier.

3. A method for treating a disease or condition associated with mitochondrial dysfunction, the method comprising an effective amount of the compound of claim 1 to a subject in need thereof.

4. The method of claim 3, wherein the effective amount is a therapeutically effective amount.

5. The method of claim 3, wherein the effective amount is a prophylactically effective amount.

6. The method of claim 3, wherein the disease is cancer.

7. The method of claim 6, wherein the cancer is T-acute lymphoblastic leukemia (T-ALL), small cell lung cancer (SCLC), non-small cell lung cancer (NSCL), glioblastoma, colorectal cancer, breast cancer, or ovarian cancer.

8. The method of claim 3, wherein the disease is a neurodegenerative disease.

9. The method of claim 8, wherein the neurodegenerative disease is Parkinson's disease, Alzheimer's disease, amyotrophic lateral sclerosis, or Huntington's disease.

10. The method of claim 3, wherein the condition is a brain condition.

11. The method of claim 10, wherein the brain condition is stroke, seizure, neuropathic pain, traumatic brain injury, spinal cord injury, aneurysm, or subarachnoid hemorrhage.

12. The method of claim 3, wherein the disease or condition is a non-neurological disorder.

13. The method of claim 12, wherein the non-neurological disorder is sepsis, acute kidney injury, cardiorenal syndrome, cardiac ischemia-reperfusion injury, pulmonary arterial hypertension, chronic obstructive pulmonary disease, or vasoconstriction.

14. The method of claim 3, wherein the condition is human aging caused by mitochondrial dysfunction.

* * * * *